US00PP26513P3

(12) United States Plant Patent
Gilmore

(10) Patent No.: US PP26,513 P3
(45) Date of Patent: Mar. 15, 2016

(54) *AGAPANTHUS PRAECOX* PLANT NAMED 'MP01'

(50) Latin Name: *Agapanthus praecox*
Varietal Denomination: MP01

(71) Applicant: Rex Gilmore, Orange, CA (US)

(72) Inventor: Rex Gilmore, Orange, CA (US)

( * ) Notice: Subject to any disclaimer, the term of this patent is extended or adjusted under 35 U.S.C. 154(b) by 93 days.

(21) Appl. No.: 14/120,034

(22) Filed: Apr. 17, 2014

(65) Prior Publication Data

US 2015/0305221 P1 Oct. 22, 2015

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Susan McCormick Ewoldt
(74) *Attorney, Agent, or Firm* — Samuel R. McCoy, Jr.

(57) ABSTRACT

'MP01' is a distinctive variety of *Agapanthus praecox*, which is characterized by green and yellow to green and white foliage variegation, a high concentrations of anthocyanin near the point of leaf attachment, a short plant height, an arched habit, more shoots per pot and more inflorescences per pot.

4 Drawing Sheets

Latin name of the genus and species: The Latin name of the novel variety disclosed herein is *Agapanthus praecox* 'MP01'.

Variety denomination: The inventive variety of *Agapanthus praecox* disclosed herein has been given the variety denomination 'MP01'.

BACKGROUND OF THE INVENTION

The present invention relates to a new and distinct variety of *Agapanthus praecox*, which has been named 'MP01'. Its market class is that of an ornamental flowering perennial. *Agapanthus praecox*, commonly called "lily of the Nile", is a flowering perennial native to South Africa that forms large clumps of dark green strap-like leaves. In summer, umbels rise above the foliage which bear numerous flowers in colors ranging from pale violet to dark purple. Its consistent size and performance, combined with its attractive inflorescences through its hardiness range make it an ideal choice for specimen, borders and mass plantings in any full to filtered sun to shady, low-maintenance landscape or container.

Parentage: The cultivar 'MP01' is a seedling selection discovered in 1988 among progeny of openly pollinated *Agapanthus praecox* (parentage unknown), sown at a wholesale nursery in Stanton, Calif. in 1987. Said seedling exhibited green and yellow foliage variegation with a distinct purple coloration at the point of leaf attachment, a short plant height, an arched habit, more shoots per pot and more inflorescences per pot when compared to the seed parent and other sibling progeny which were taller, had fewer shoots and inflorescence per pot and did not exhibit variegated foliage. This variegated plant was isolated for further observation. Said plant was further grown and asexually propagated through many generations from 1988 until 2013, at which time it was determined that the characteristics for which it was originally selected were uniform and stable. The new plant was given the name 'MP01'.

Asexual Reproduction: 'MP01' was first asexually propagated by dividing the root-bearing, rhizomatous propagules of the plant (i.e. "division cloning") in 1988 in Stanton, Calif. and has since been asexually propagated through many subsequent generations. The distinctive characteristics of the inventive 'MP01' variety are stable from generation to generation; clones of the variety produced by asexual reproduction maintain the distinguishing characteristics of the original plant.

SUMMARY OF THE INVENTION

'MP01' is a distinctive variety of *Agapanthus praecox*, which is characterized by green and yellow to green and white foliage variegation, a high concentrations of anthocyanin near the point of leaf attachment, a short plant height, an arched habit, more shoots per pot and more inflorescences per pot.

DETAILED BOTANICAL DESCRIPTION OF THE VARIETY

Figure 1:
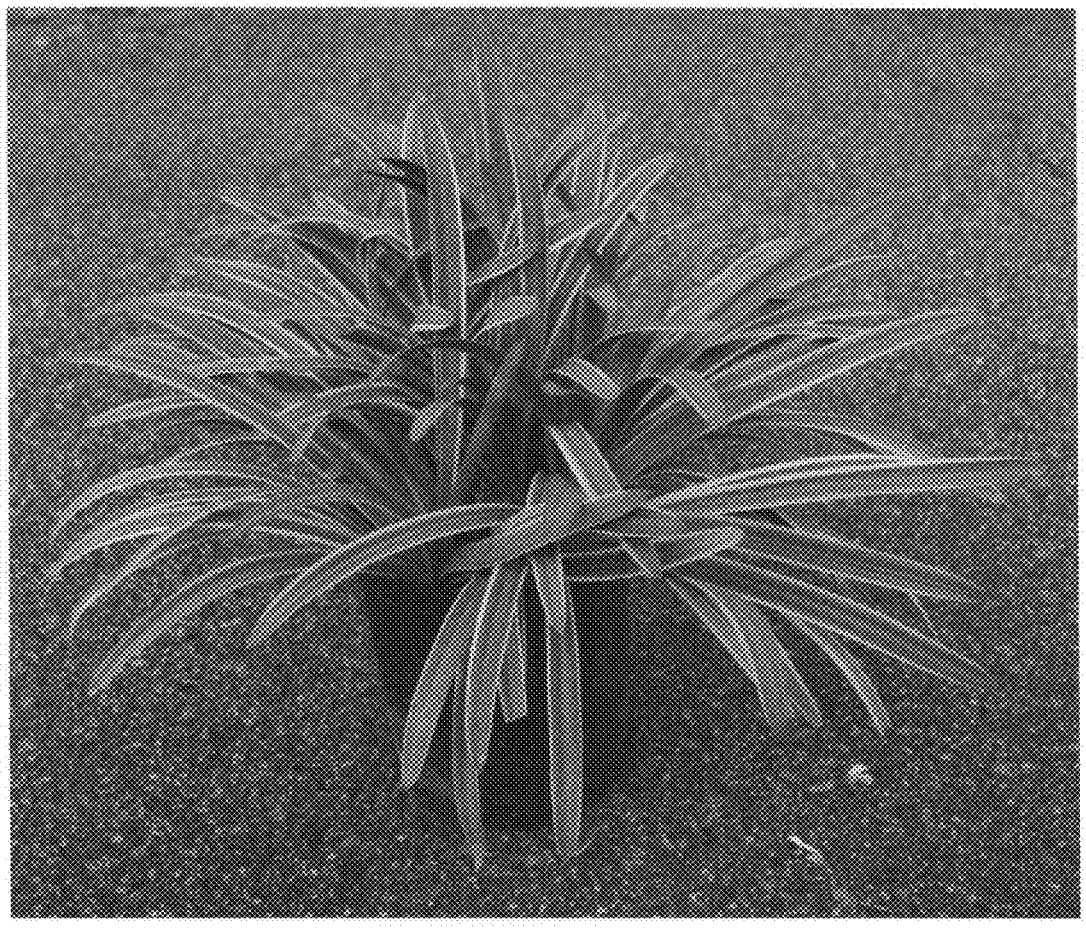
FIG. 1 shows an exemplary 'MP01' specimen, approximately 7 months of age, grown in a 15 cm nursery pot.
Figure 2:
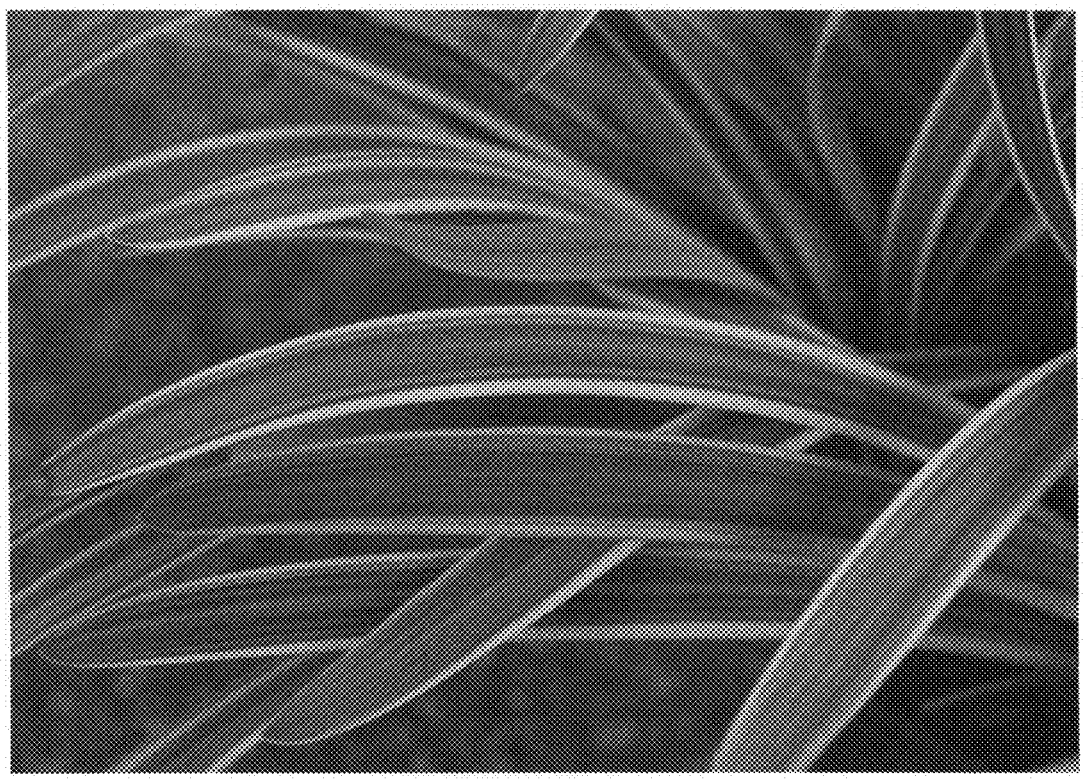
FIG. 2 shows the array of foliage variegation combinations of 'MP01'.
Figure 3:
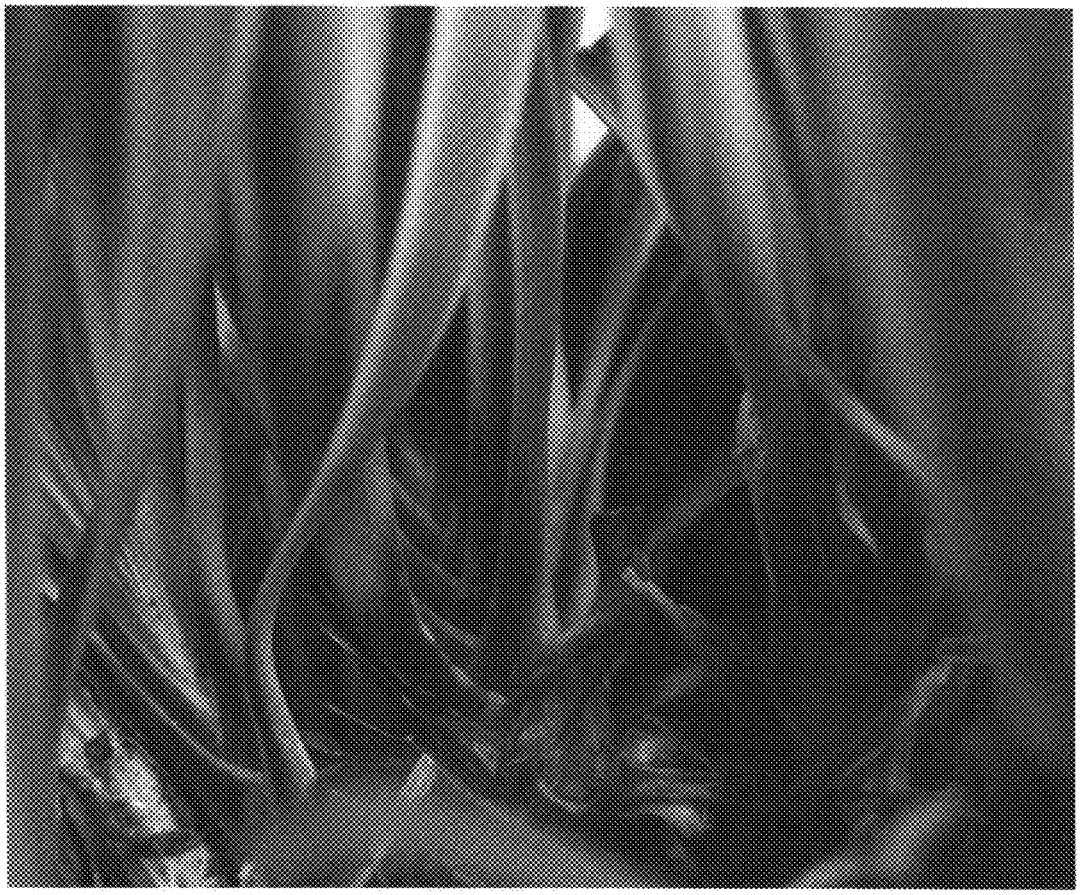
FIG. 3 shows the distinct purple coloration near the point of leaf attachment.
Figure 4:
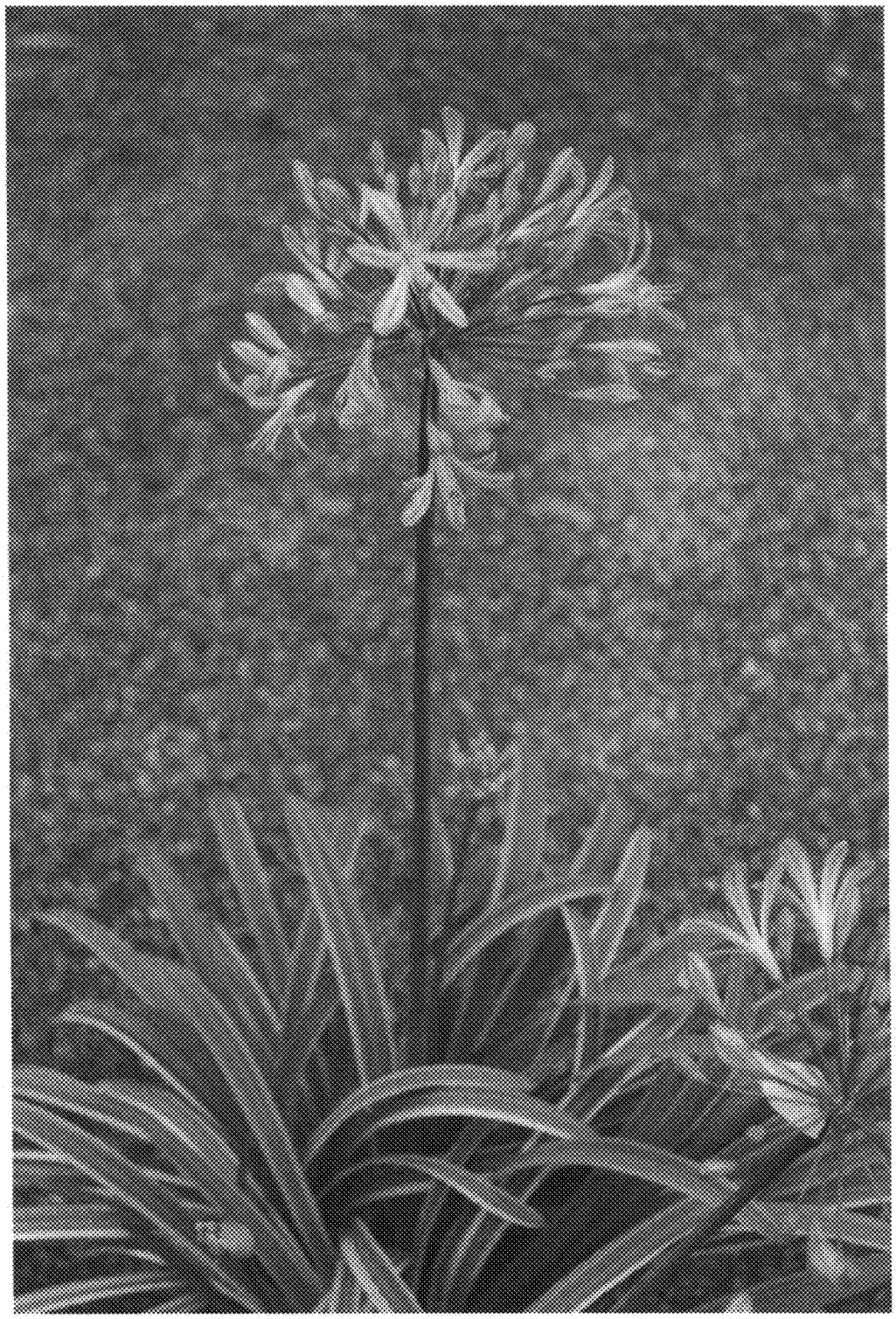
FIG. 4 shows an exemplary 'MP01' inflorescence.

The following is a detailed botanical description of a new and distinct variety of *Agapanthus praecox* known as 'MP01'. Unless indicated otherwise, the descriptions disclosed herein are based upon observations made in January 2014 of mature 'MP01' plants, approximately 7 months of age, grown in soilless potting media in 15 cm nursery pots. Plants were grown in full sun; fertilized with slow release granular fertilizer and regularly watered with overhead irrigation. No pest or disease measures were taken during production.

Those skilled in the art will appreciate that certain characteristics will vary with older or, conversely, with younger plants. 'MP01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 1986 edition. Note that generic color descriptions such as "green" do not exist in the R.H.S. charts and the corresponding R.H.S. colors are quoted.

The distinguishing features and other characteristics of *Agapanthus praecox* 'MP01' are apparent from the description provided below.

Growth Habit, Dimensions and Color

Plant description:

*Plant habit.*—Rhizomatous herbaceous perennial with an arching habit.

*Height.*—29 cm to the tallest leaf with the majority of foliage at or below 23 cm, as measured; may reach 40 cm at maturity.

*Width.*—53 cm, as measured.

*Bloom period.*—Summer.

*Hardiness.*—USDA Zone 9 to 10.

*Environmental tolerances.*—Prefers to be grown in full sun. Drought tolerant once established; moderate to good recovery with watering after severe wilting. Tolerates a wide range of soil types from sandy loam to loamy clay.

*Pest and disease susceptibility or resistance.*—In common with the species, none of note.

*Propagation.*—Propagation is accomplished through division of rhizomes.

*Time to initiate roots.*—Approximately 3 weeks.

*Crop time.*—Depending on latitude of and microclimate of growing location, a fully rooted cutting requires approximately 3 months with an additional 5 to 7 months needed to produce a mature and marketable 15 cm container.

Roots: The roots are fibrous and freely-branched, colored white, fleshy, similar to other *Agapanthus*; high root density.

Stem:

*Branching habit.*—Acaulescent, rhizomatous plant with shoots emerging from rhizomes with an upright attitude.

Basal shoots:

*Shoots density.*—11 divisions, or propagules, per 15 cm nursery pot, with the oldest propagules near the center of the plant's crown possessing 17 leaves and shoots of varying ages and sizes.

*Shoot strength.*—Medium.

*Cross section.*—Concave.

*Shoot color* (*adaxial surfaces*).—Variegated; comprised of relatively wide yellow-green (RHS 145B) striations at the margin and a combination of relatively fine striations of yellow-green (RHS 147B), green (RHS 138B), and yellow-green (RHS 145B) covering the remainder of the leaf surface; shoot becoming solid yellow-green (RHS 145D) at the base.

*Shoot color* (*abaxial surfaces*).—Variegated; comprised of relatively wide yellow-green (RHS 145B) striations at the margin and a combination of relatively fine striations of yellow-green (RHS 147B) and green (RHS 138B) covering the remainder of the leaf surface; shoot becoming solid yellow-green (RHS 145D) at the base.

*Shoot surface texture.*—Smooth.

Foliage:

*Type.*—Evergreen.

*Arrangement.*—Basal.

*Division.*—Simple.

*Attitude.*—Pendulous and slightly curled.

*Shape.*—Linear.

*Apex.*—Acute.

*Base.*—Sheathed.

*Cross section.*—Concave.

*Venation.*—Parallel.

*Vein color* (*adaxial surfaces*).—Same as surrounding foliage.

*Vein color* (*abaxial surfaces*).—Same as surrounding foliage.

*Margins.*—Entire.

*Attachment.*—Acaulescent.

*Texture.*—Smooth and glossy.

*Surface hairiness* (*adaxial surface*).—Glabrous.

*Surfaces hairiness* (*abaxial surface*).—Glabrous.

*Mature leaf dimensions.*—Longest observed leaf measuring length 29 cm, average width 1.6 cm at widest point.

*Mature leaf color* (*adaxial & abaxial surface*).—Variegated and glaucous; comprised of relatively wide yellow (RHS 8B) striations at the margin which become yellow (RHS 8C) with age, and a combination of relatively fine striations of green (RHS 138A), green (RHS 138B), and green (RHS 138C) covering the remainder of the leaf surface; shoot becoming solid yellow-white (RHS 158D) near the leaf base. A high concentration of anthocyanin is present at and near the point of leaf attachment which creates a general purple appearance, corresponding closest to RHS Purple 79A.

*Petiole.*—Leaves are acaulescent; sessile.

*Stipules.*—Absent.

Inflorescence:

*Inflorescence type.*—Umbellate.

*Umbel diameter.*—Largest observed is 15 cm wide.

*Number of umbels per pot.*—Potentially one inflorescence per division; 11 propagules will yield 11 inflorescences.

*Number of flowers per umbel.*—Ranging from 35 to 60 flowers.

*Scape dimensions.*—Ranging from 35 to 45 cm long and 5 to 7 mm wide at the base.

*Other characteristics of scape.*—Color is yellow green (RHS 144A); cylindrical shape; texture is smooth; glabrous.

Buds:

*Bud shape.*—Obelliptic; apex round; base cuneate.

*Bud dimensions.*—24 mm long and 7 mm wide, prior to anthesis.

*Bud color.*—Striations of violet-blue (RHS 91A) and violet-blue (RHS 91D).

*Bud texture.*—Glabrous.

Flowers:

*General.*—Apetalous flowers; shape is campanulate; self-cleaning and non-fragrant. Attitude is upward and outward. Bloom period is spring and summer.

*Pedicel dimensions.*—Ranges from 37 mm to 62 mm, as measured.

*Pedicel color.*—Yellow green (RHS 144B).

*Pedicel surface.*—Glabrous.

*Perianth dimensions.*—Approximately 27 mm wide and 25 mm long, at anthesis.

*Tepals.*—Six basally fused tepals.

*Tepal shape.*—Oblanceolate; apex is round.

*Tepal dimensions.*—37 mm long and 8 mm wide, as measured.

*Tepal color.*—Violet-blue (RHS 92B) at both the midrib and margins with violet-blue (RHS 91D) in areas between margins and midrib; colors are the same for both the adaxial and abaxial surfaces.

*Tepal surface.*—Smooth; glabrous.

*Tepal margin.*—Entire.

Reproductive organs:

*Stamens.*—Six.

*Stamen attachment.*—Each is adnate to a corresponding tepal.

*Filament color.*—Violet-blue 91D at base, becoming violet-blue 92C near apex.

*Filament dimensions.*—26 mm long and less than 1 mm wide.

*Anther attachment.*—Versatile.

*Anther dimensions.*—1.5 to 2 mm.

*Anther color.*—Black (RHS 202A).

*Pollen.*—Present; low quantity; color appears to be green-yellow, approximating to RHS 1C.

*Pistil.*—One.

*Pistil dimensions.*—21 mm long, from apex of ovary; width is less than 1 mm.

*Pistil color.*—Violet-blue 91D at base, becoming violet-blue 92C near apex.

*Ovary shape.*—Oblong.

*Ovary color.*—Yellow-green (RHS 145B).

*Ovary dimensions.*—12 mm long and 2.5 mm wide.

*Ovary position.*—Superior.

Fruit and seeds: Not observed to date.

Comparisons with Other *Agapanthus*

The seed parent, *Agapanthus praecox*, is characterized by a larger overall plant size, a weeping habit, broad leaves and an absence of variegation and anthocyanin at the point of leaf attachment. By comparison, 'PM01' is a smaller plant with an arched habit, and green to white to yellow leaf variegation as described herein, and a high concentration of anthocyanin at the point of leaf attachment. Furthermore, 'MP01' exhibits improved plant vigor and a higher number of inflorescences.

There are three cultivars of *Agapanthus praecox* known to the inventor which are suited for comparison to 'MP01': *Agapanthus praecox* 'Tinker Bell' (unpatented), *Agapanthus praecox* 'Silver Streak' (unpatented), *Agapanthus praecox* 'variegata' (unpatented). All three of these cultivars exhibit similar leaf variegation colors and patterns to 'MP01' but 'MP01' can be distinguished by one or more characteristics.

'Tinker Bell' is roughly the same size as 'MP01' and has similar variegation, however 'Tinker Bell' has broader foliage measuring approximately 25 mm wide compared to the foliage of 'MP01' which measures 16 mm wide. 'Tinker Bell' exhibits less plant vigor and fewer blooms compared to 'MP01' and also lacks the purple coloration at the point of leaf attachment seen in 'MP01'.

'Silver Streak' has broader, undulating and curled foliage that is approximately 38 mm wide whereas 'MP01' has fine foliage of approximately 16 mm wide that lacks undulation and curling. The variegation pattern of 'Silver Streak' is distinct from that of 'MP01', with wide yellow-white striations at the margins and green striated coloration across the remainder of the foliage. Scapes of 'Silver Streak' are much taller, measuring up to 120 cm whereas the scapes of 'MP01' measure to approximately 60 cm. 'Silver Streak' lacks the purple coloration at the point of leaf attachment seen in 'MP01'.

*Agapanthus praecox* 'Variegata' is a larger plant with taller scapes and larger umbels compared to 'MP01'. 'Variegata' also lacks the purple coloration at the point of leaf attachment seen in 'MP01'.

That which is claimed is:

1. A new and distinct variety of *Agapanthus praecox* plant named 'MP01', substantially as described and illustrated herein.

* * * * *